USO11382784B2

(12) United States Patent
Vogel et al.

(10) Patent No.: US 11,382,784 B2
(45) Date of Patent: Jul. 12, 2022

(54) JOINT FOR AN ORTHOPEDIC DEVICE

(71) Applicant: OTTOBOCK SE & CO. KGAA, Duderstadt (DE)

(72) Inventors: Carsten Vogel, Duderstadt (DE); Matthias Schilling, Weissenborn-Luderode (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 262 days.

(21) Appl. No.: 16/323,920

(22) PCT Filed: Jul. 5, 2017

(86) PCT No.: PCT/EP2017/066824
§ 371 (c)(1),
(2) Date: Apr. 4, 2019

(87) PCT Pub. No.: WO2018/028891
PCT Pub. Date: Feb. 15, 2018

(65) Prior Publication Data
US 2020/0383814 A1 Dec. 10, 2020

(30) Foreign Application Priority Data
Aug. 10, 2016 (DE) .................. 102016114834.2

(51) Int. Cl.
*A61F 5/56* (2006.01)
*A61F 5/01* (2006.01)
(52) U.S. Cl.
CPC .... *A61F 5/0125* (2013.01); *A61F 2005/0155* (2013.01); *A61F 2005/0158* (2013.01);
(Continued)

(58) Field of Classification Search
CPC ............ A61F 5/0125; A61F 2005/0155; A61F 2005/0158; A61F 2005/0162;
(Continued)

(56) References Cited

U.S. PATENT DOCUMENTS 5,873,847 A 2/1999 Bennett et al.
6,471,664 B1 10/2002 Campbell et al.
(Continued)

FOREIGN PATENT DOCUMENTS

| CN | 201745635 | 2/2011 |
| RU | 2596871 C1 | 9/2016 |
| SU | 925337 A1 | 5/1982 |

OTHER PUBLICATIONS

PCT International Search Report for PCT International Patent Application No. PCT/EP2017/066824, dated Sep. 15, 2017.
(Continued)

*Primary Examiner* — Tarla R Patel
(74) *Attorney, Agent, or Firm* — Holland & Hart LLP

(57) ABSTRACT

A joint for an orthopedic device which has a first articulated arm and a second articulated arm, which are mounted about a swivel axis such that they can be swiveled relative to one another, and a blocking device which can be moved into a release position and a blocking position. The blocking device, when in the blocking position, blocks the swiveling of the first articulated arm relative to the second articulated arm in the first swivel direction, independently of a swivel angle between the first articulated arm and the second articulated arm, insofar as the swivel angle is in a predetermined range, and allows the swiveling in the first swivel direction, insofar as the swivel angle is outside of the predetermined range.

16 Claims, 10 Drawing Sheets

(52) U.S. Cl.
CPC ............ *A61F 2005/0162* (2013.01); *A61F 2005/0179* (2013.01)

(58) Field of Classification Search
CPC ........ A61F 2005/0179; A61F 2005/016; A61F 2005/0169; A61F 5/0123; A61F 5/0102; A61F 5/01; A61F 5/00
See application file for complete search history.

(56) References Cited

U.S. PATENT DOCUMENTS

| | | | |
|---|---|---|---|
| 7,517,330 B2 | 4/2009 | Deharde et al. | |
| 7,662,118 B2 | 2/2010 | Pansiera | |
| 7,935,153 B2 | 5/2011 | Auberger | |
| 8,715,367 B1 | 5/2014 | Pansiera et al. | |
| 2002/0169402 A1 | 11/2002 | Hatton et al. | |
| 2004/0049140 A1* | 3/2004 | Doty | A61F 5/0123 602/16 |
| 2006/0211966 A1 | 9/2006 | Hatton et al. | |
| 2007/0270976 A1 | 11/2007 | DeHarde et al. | |
| 2010/0022929 A1 | 1/2010 | Pansiera et al. | |
| 2011/0009786 A1* | 1/2011 | Chan | A61F 5/0125 602/16 |
| 2011/0251539 A1 | 10/2011 | Gentz et al. | |
| 2014/0350447 A1 | 11/2014 | Brass | |
| 2015/0018735 A1* | 1/2015 | Chetlapalli | A61F 5/0123 602/16 |
| 2016/0058596 A1* | 3/2016 | Chiang | A61F 5/0123 602/16 |
| 2016/0151190 A1 | 6/2016 | Lurssen et al. | |
| 2016/0361189 A1* | 12/2016 | Campbell | A61F 5/0125 |
| 2017/0000639 A1* | 1/2017 | Costello | A61F 5/0125 |

OTHER PUBLICATIONS

Office Action issued in Chinese Patent Application No. 201780048381.2, 9 pgs.

* cited by examiner

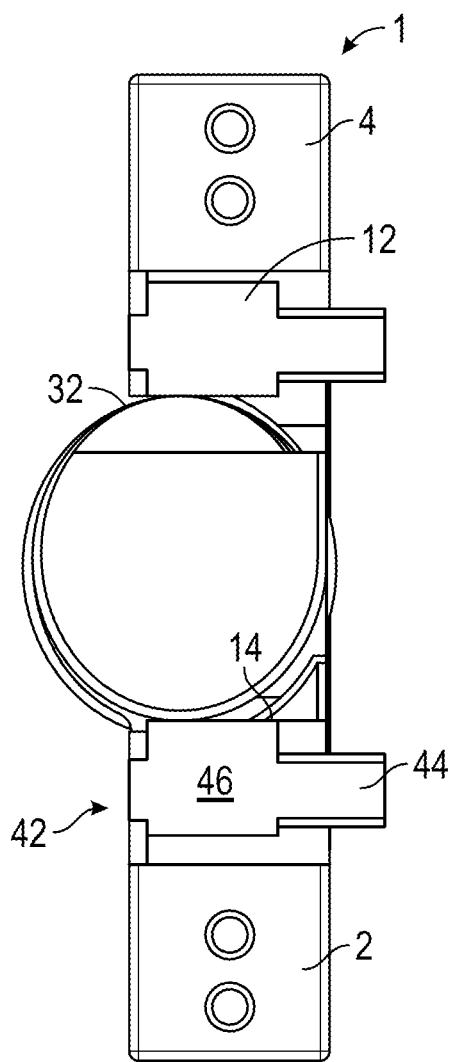 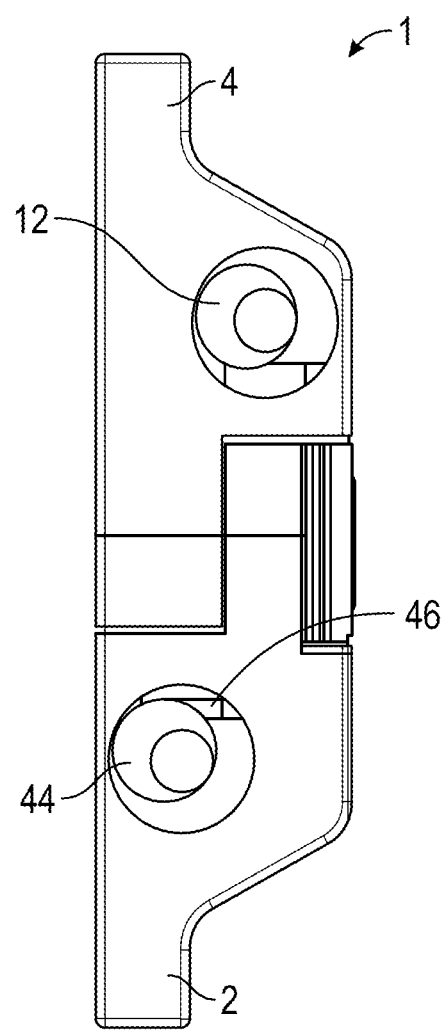
FIG. 9A                    FIG. 9B

JOINT FOR AN ORTHOPEDIC DEVICE

TECHNICAL FIELD

The invention relates to a joint for an orthopedic device which has a first articulated arm and a second articulated arm, which are mounted about a swivel axis such that they can be swiveled relative to one another, and a blocking device which can be moved into a release position and a blocking position.

BACKGROUND

This type of joint is known, for example, from U.S. Pat. No. 7,517,330 B2 and U.S. Pat. No. 7,662,118 B2. They are used, for example, as a joint for orthoses, such as knee orthoses; however, they can also be used in other orthoses or orthopedic devices. The first articulated arm and the second articulated arm are mounted about a swivel axis such that they can be swivelled relative to one another. They are to be swiveled across a swivel range which is generally restricted by two limit stops, each of which restrict the possibility of movement in one of the two opposing swivel directions. When the blocking device is in the release position, the two articulated arms can generally be freely swiveled towards one another in both swivel directions within the swivel range. However, if the blocking device is in the blocking position, a swiveling of the two articulated arms relative to one another is prevented in a first swivel direction. In the prior art, this is achieved, for instance, by two components—which are both equipped with ratchets or tilted teeth—engaging with each other. The ratchet-like teeth prevent a further swiveling in the first swivel direction, but allow for a swiveling in the opposite second swivel direction, as the teeth are beveled on this side and can slide over one another. However, a swiveling of the two articulated arms relative to one another in the second swivel direction, which is also possible when the blocking device is in the blocking position, stops if one of the two articulated arms strikes the second limit stop in such a way that a further swiveling in the second swivel direction is no longer possible either. In this state, the joint is completely blocked and the two articulated arms can no longer execute a swivel movement relative to one another.

U.S. Pat. No. 8,715,367 B1 describes a joint according to the preamble, the blocking device of which, when in the blocking position, blocks a swiveling of the two articulated arms relative to one another in the first swivel direction, independently of the angle at which the two swivel arms are situated relative to one another.

A joint according to the preamble may be used, for example, in a knee orthosis. The knee is generally blocked as the blocking device is in the blocking position by default and the knee is fully extended such that one of the two articulated arms lies on the second limit stop. A movement of the articulated arms in the first swivel direction is thus prevented by the blocking device and a movement of the articulated arms in the second swivel device by the respective second limit stop. However, if the wearer of this type of knee orthosis wishes to sit down, for instance, it is beneficial to be able to bend the knee. In order to achieve this, the blocking device is moved from the blocking position into the release position, such that the two articulated arms can be swiveled relative to one another. The blocking device is subsequently moved back into the blocking position or moves back into this position by itself. If the wearer of an orthosis with this type of joint then stands up and fully extends the leg, such that one of the two articulated arms lies on the second limit stop, the joint is once again completely blocked and can be safely subjected to a load. However, if the wearer of this orthosis stands up and the joint is not, for example, fully extended, it is important to ensure that the movement in the first swivel direction, which corresponds to a flexion of the joint, is reliably prevented, for instance if the joint is subjected to a load, i.e. if a torque acts about the swivel joint on one of the two articulated arms. As previously explained, this is achieved in the prior art by toothing systems which engage with each other. However, on the one hand, this has the disadvantage that an actual latching and blocking of the swivel movement in the first swivel direction can only be achieved at certain angle positions, namely when the teeth interlock exactly. On the other hand, as a result of the teeth sliding over each other, a rattling or clicking sound occurs, which is deemed unpleasant and disruptive.

SUMMARY

The invention therefore aims to improve a joint in such a way that the disadvantages named are avoided or at least mitigated.

The invention solves the task at hand by way of a joint which is characterized by the fact that the blocking device, when in the blocking position, blocks the swiveling of the first articulated arm relative to the second articulated arm in the first swivel direction, independently of a swivel angle between the first articulated arm and the second articulated arm, insofar as said swivel angle is in a predetermined range, and allows the swiveling in the first swivel direction, insofar as the swivel angle is outside of the predetermined range. In contrast to joints known from the prior art, this results in the prevention of a swiveling of the two articulated arms relative to one another in the first swivel direction at not only a few discreet points, namely when the toothing systems of the interlocking components engage precisely, but rather independently of the swivel angle between the two articulated arms, insofar as this swivel angle lies in a predetermined range. If the swivel angle lies outside of the predetermined range, the movement of the two articulated arms relative to one another is not impaired in the first swivel direction.

This increases the level of comfort when wearing an orthopedic device that features a joint according to the invention. In contrast to the prior art, in which a swiveling in the first swivel direction may still occur until the toothing systems of the two interlocking components fit precisely, this unwanted short-term swiveling cannot occur with a joint according to the invention. Independently from the swivel angle between the two articulated arms, according to the invention, the further swiveling is always prevented in the first direction insofar as the swivel angle lies within the predetermined range. This also avoids potential disruptive rattling or clicking noises known from the prior art such that on the one hand, no disruptive noises occur and on the other hand, an orthopedic device, which for example is worn under normal clothing, is not recognised as an orthopedic device, or at least not immediately.

A contact surface is preferably arranged on the first articulated arm, which can come into contact with a blocking element, which is moveably arranged on the second articulated arm. This contact can occur if the blocking device is in the blocking position. In a preferred configuration, the contact between the blocking element and the contact surface prevents a swiveling of the first articulated arm relative to the second articulated arm in the first swivel direction.

In this case, it is very possible that the blocking element can only come into contact with the contact surface in the predetermined range of the swivel angle between the two articulated arms, and that such contact does not occur at swivel angles that do not lie in the predetermined range.

The contact surface is fixed on the first articulated arm such that it cannot be oved. This means that it follows every movement of the first articulated arm. The first articulated arm preferably has a widened end piece that extends around the swivel axis in a preferred configuration. The contact surface is preferably arranged on a radially external peripheral surface of this end piece.

If the blocking element is designed as a cam that is mounted in a guide such that it can be moved or as a similar moveably mounted element, the blocking element itself may comprise a close-fit area which is intended to lie closely on the contact surface. This is preferably be equipped with an anti-slip coating. The guide itself may be configured to be tangential to the circular or almost circular widened end piece of the first articulated arm such that a gap emerges between the radially external contact surface of this end piece and the inner surface of the guide, which faces away from said contact surface, wherein the cam is situated in the gap. This gap has a variable width and in particular is designed in such a way that it becomes narrower in one direction but widens or remains the same in the other direction. Here, it has been proven advantageous if the width of this gap becomes so narrow that it is smaller than the width of the moveably mounted cam.

In this case, if the blocking device is in the blocking position, the cam comes into contact with the contact surface. A further swiveling of the first articulated arm relative to the second articulated arm in the first swivel direction would cause the cam to follow the movement of the contact surface relative to the second articulated arm, due to the contact with the contact surface, and it would have to be moved into the area of the gap which is too narrow for the cam. This would result in a clamping effect which prevents a further movement of the articulated arm in the first swivel direction. Given that the width of the gap decreases in this direction, the effect is also self-amplifying. The stronger a torque acting on the articulated arms, wherein this torque would result in a swiveling of the two articulated arms relative to one another in the first swivel direction, the stronger the blocking effect of the blocking device designed in this way.

However, a swiveling of the two articulated arms in the opposite second swivel direction can occur without difficulty as the cam, when in contact with the contact surface, is moved in the other direction in which the gap widens or in which the width of the gap remains constant. The width is sufficient to move the cam such that a swiveling in this direction can occur without difficulty.

In an alternative configuration, the blocking element is an eccentrically mounted pin, bolt or cylinder. In this configuration, the blocking element has a longitudinal axis parallel to which it is eccentrically mounted. The lateral surface of this blocking element comes into contact with the contact surface of the blocking device insofar as the blocking device is in the blocking position. As a result of the eccentric mounting of the blocking element, the distance of the external lateral surface of the blocking element from the bearing axis is not constant across the periphery, but rather has a minimum and a maximum. Should the distance of the contact surface that is arranged on the first articulated arm now change relative to the bearing axis of the blocking element, the blocking element rotates about its bearing axis, for instance under the influence of gravity, until the lateral surface of the blocking element lies on the contact surface. In this configuration, it is advantageous if the contact surface on the first articulated arm is designed such that it is at a different distance to the bearing axis of the blocking element at different swivel angles, i.e. angles between the first articulated arm and the second articulated arm.

The blocking element is preferably preloaded towards the contact surface. The blocking element is preferably preloaded by a spring element or the weight force acting on the blocking element. Of course, there are other preloading possibilities which are advantageous for different configurations. An expert will have no difficulties in selecting a suitable preloading method for a particular shape of the blocking element.

It has been proven advantageous if the contact surface is designed to be eccentric in relation to the swivel axis. This means that the distance of the contact surface relative to the swivel axis is not constant across the periphery.

The joint preferably has an activation element, the activation of which causes a movement of the blocking device from the blocking position into the release position. A swivel range in which the first articulated arm can be swiveled relative to the second articulated arm preferably extends from a first limit stop to a second limit stop, wherein the predetermined range is smaller than this swivel range. This means in particular that there is part of the swivel range in which a swivel movement of the two articulated arms relative to one another in the first swivel direction is not blocked if the blocking device is in the blocking position. This only occurs within the predetermined range which, in this example of an embodiment, is smaller than the swivel range. It is especially preferable if the predetermined range in a second swivel direction is restricted by the second limit stop, this second swivel direction being the opposite direction to the first swivel direction. In this case it is possible to completely block the joint if the blocking device is in the blocking position and the respective articulated arm lies on the second limit stop.

In a preferred configuration, the joint also has a second blocking device which can be moved into a release position and a blocking position, in which it blocks the swiveling of the first articulated arm relative to the second articulated arm in the second swivel direction, which is opposite to the first swivel direction, independently of a swivel angle between the first articulated arm and the second articulated arm, insofar as said swivel angle is in a predetermined range, and allows the swiveling in the second swivel direction, insofar as the swivel angle is outside of the predetermined range.

This creates a joint which has two possible ranges for each swivel direction. In one of the two ranges, the swiveling in the respective swivel direction is enabled by the blocking device, whereas in the other it is prevented. Given that each blocking device preferably does not impair the movement in the respective other swivel direction, the swivel capacity of both articulated arms is almost completely freely adjustable.

The predetermined range and the second predetermined range can be individually adjusted across the selected contour of the contact surface that comes into contact with the blocking element of the respective blocking device so as to avoid a further swiveling in one of the two swivel directions. In principle, it is also possible to provide several ranges for a blocking device in which, for example, a swiveling is permitted.

BRIEF DESCRIPTION OF THE DRAWINGS

In the following, an example of an embodiment of the present invention will be explained in more detail by way of the attached drawings: They show FIG. 1—a schematic top view of a joint according to a first example of an embodiment of the present invention, FIGS. 2 to 5—a sectional view through the joint shown in FIG. 1 in different positions, FIGS. 6a to 6c—two views of a joint according to another example of an embodiment of the present invention in different positions, FIG. 7—the schematic depiction of a joint according to another example of an embodiment, FIG. 8—the depiction of a further joint according to an example of an embodiment of the present invention and FIGS. 9a and 9b—two views of a joint according to another example of an embodiment of the present invention.

DETAILED DESCRIPTION

Figure 1:
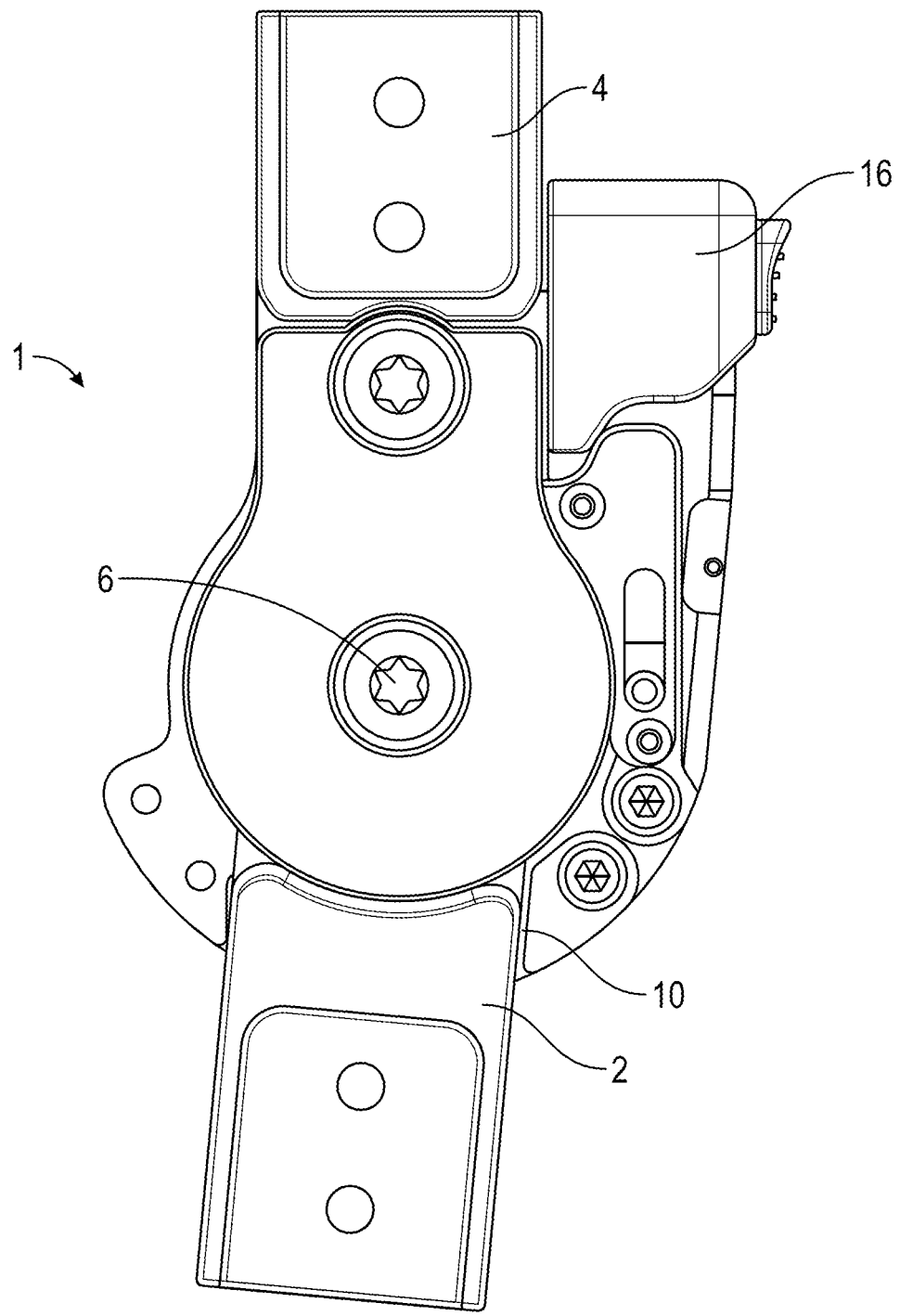

FIG. 1 depicts a joint 1 according to a first example of an embodiment of the present invention. It comprises a first articulated arm 2 and a second articulated arm 4 which are mounted about a swivel axis such that they can be swiveled relative to one another. The swivel range across which such a swiveling is possible is restricted by a first limit stop 8, not depicted in FIG. 1, and a second limit stop 10. Inside the joint 1 shown in FIG. 1 is a blocking element 12 and a contact surface 14, which are depicted in FIGS. 2 to 5. The position of the blocking element 12 can be changed by way of an activation element 16, causing the blocking device to move from the blocking position into the release position. To this end, the activation element 16 in FIG. 1 in the example of an embodiment depicted must be moved upwards.

Figure 2:
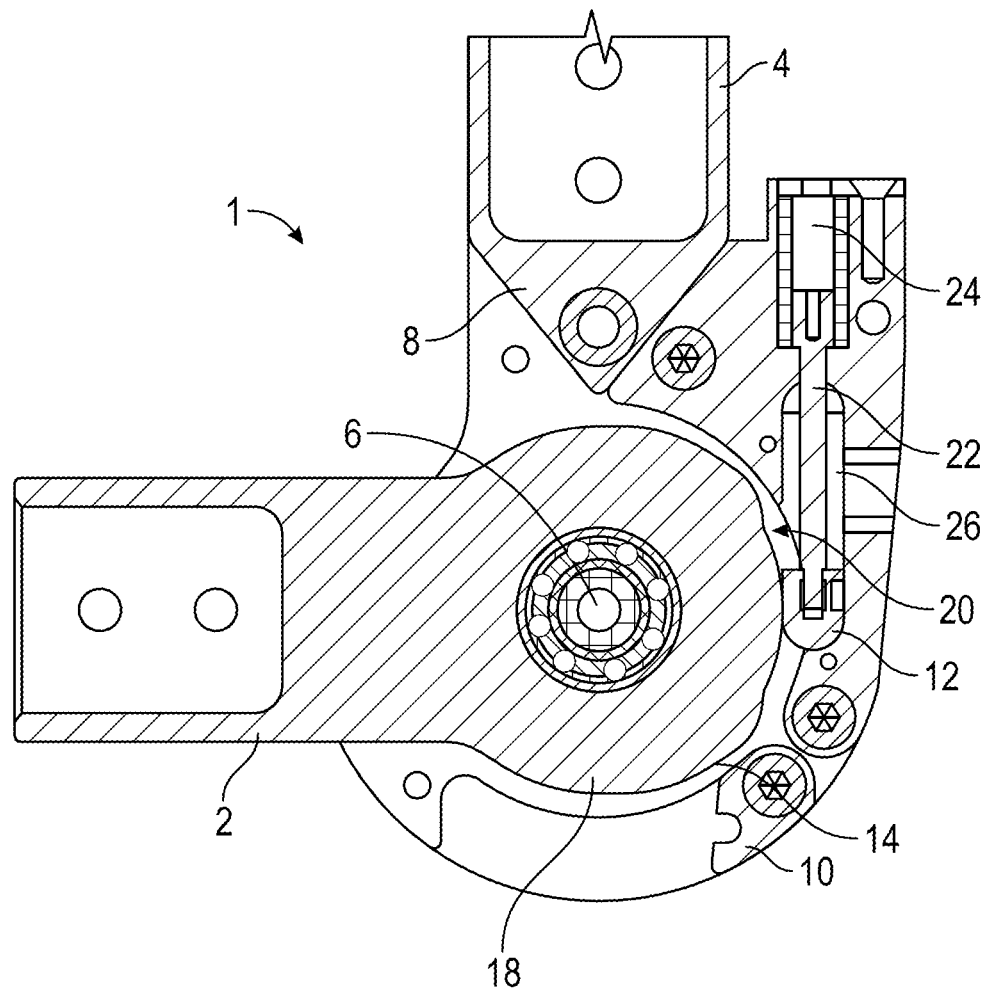

FIGS. 2 to 5 show a sectional view through the joint 1 shown in FIG. 1. In figure the first articulated arm 2 has been swiveled relative to the second articulated arm 4 in contrast with figure. The first articulated arm 2 has an end piece 18 which extends around the swivel axis 6. The contact surface 14, which is not engaging with the blocking element 1 in the situation shown in FIG. 2, is located in the radially external area of this end piece 18.

The radial distance of the contact surface 14 from the swivel axis 6 is not constant across the periphery, as is made clear in FIG. 2. The end piece 18 comprises a flattened area 20, in which the distance of the contact surface 14 from the swivel axis 6 is smaller than in the remaining area. This is why, when the two articulated arms 2, 4 are positioned relative to one another in the angle position shown in FIG. 2, the contact surface 14 does not engage with the blocking element 12.

The joint 1 is thus in a position in which a swiveling of the first articulated arm 2 relative to the second articulated arm 4 is possible in both the first and second swivel direction, although the blocking device is in the blocking position.

The blocking element 12 is situated on a pin 22, which is spring-loaded by a spring 24 that pushes it (the pin) downwards in FIG. 2. The blocking element 2 is thus also pushed downwards, meaning that the blocking device is preloaded in the blocking position. The pin 22 can be moved upwards by way of the activation element 16, not depicted in FIG. 2, thereby causing the blocking element 12 to move upwards inside a guide 26. This allows the blocking device to be moved from the blocking position into the release position.

In FIG. 2, the first limit stop 8 can also be seen alongside the second limit stop 10; the first limit stop restricts the potential swivel movement. The design of the first limit stop 8 and the second limit stop 10 allows for the restriction of the maximum swivel range.

Figure 3:
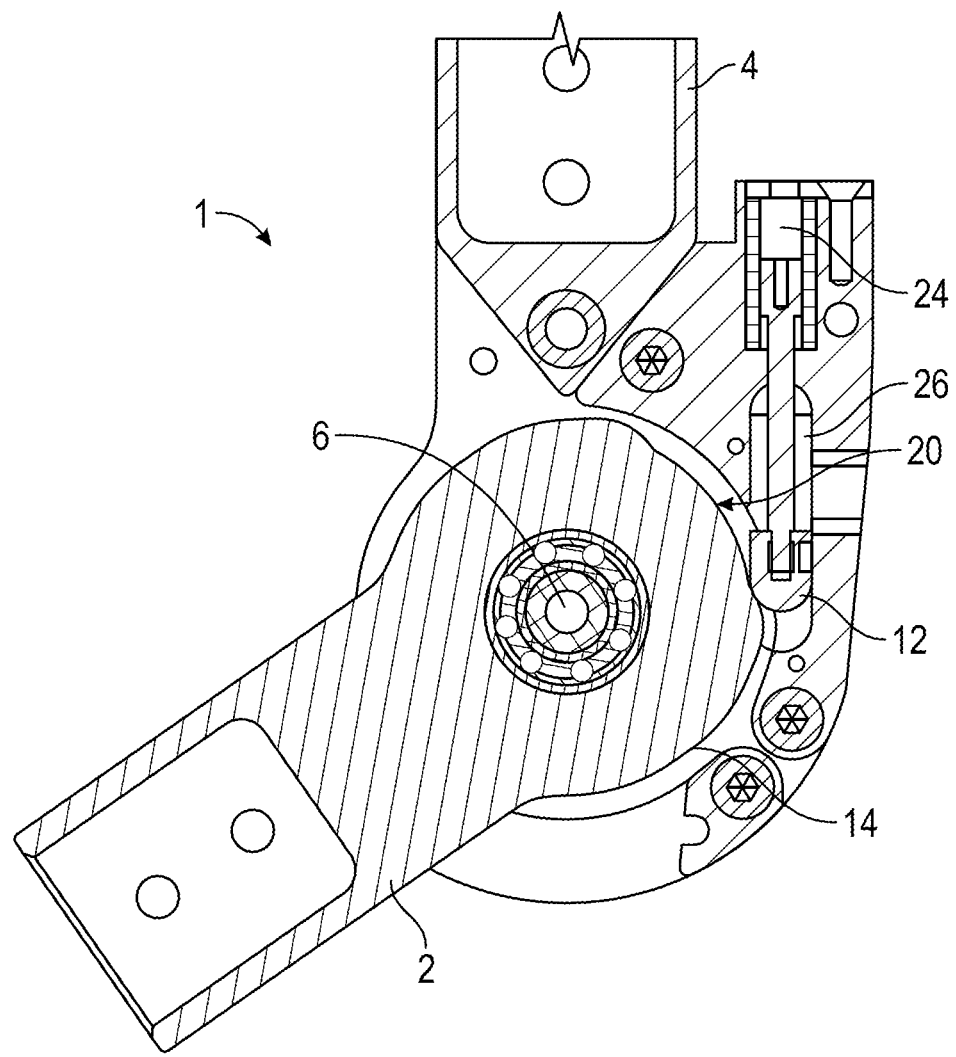

In FIG. 3, the first articulated arm 2 has been swiveled relative to the second articulated arm 4 in the direction of the extension of the joint 1. The contact surface 14 now comes into contact with the blocking element 12 with an area in which the distance between the contact surface 14 and the swivel axis 6 is considerably larger than in the flattened area 20. In contrast to FIG. 2, this causes the blocking element 12 to be moved upwards, causing the spring 24 to compress. However, this movement is possible against the force of the spring 24, meaning that a swiveling of the first articulated arm 2 relative to the second articulated arm 4 in the direction of extension is possible. A further swiveling of the first articulated arm 2 relative to the second articulated arm 4 in the direction of flexion would also be possible at the swivel angle between the first articulated arm 2 and the second articulated arm 4 depicted in FIG. 3 given that the blocking element 12 can be moved downwards in the guide 26.

Figure 4:
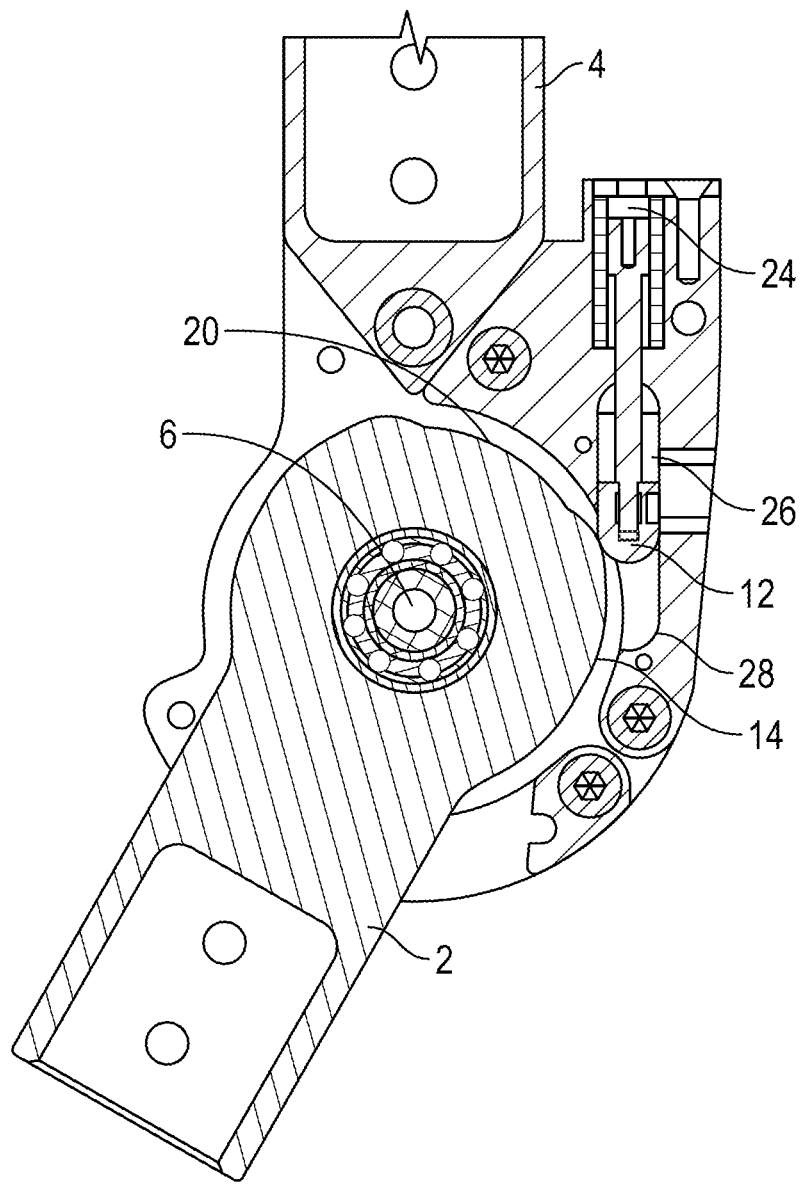

FIG. 4 depicts the situation in which the first articulated arm 2 has been swiveled even further relative to the second articulated arm 4 in the direction of extension. The contact surface 14 is now in contact with the blocking element 12, which has been moved down further in the guide 26 against the force of the now very compressed spring 24. The flattened area 20 now no longer provides any room for the blocking element 12 to move. In the area in which the contact surface 14 comes into contact with the blocking element 12, the distance between the contact surface 14 and the swivel axis 6 is so great that a slit that occurs between the contact surface 14 and an external wall 28 of the guide 26 is not wide enough to accommodate the blocking element 12.

A further swiveling of the first articulated arm 2 relative to the second articulated arm 4 in the direction of extension is therefore possible as the blocking element 12 can be moved further upwards in the guide 26. However, an opposing swiveling of the first articulated arm 2 relative to the second articulated arm 4 in the direction of flexion is blocked by the blocking device because, as a result of the contact between the contact surface 14 and the blocking element 12 during this swiveling, the blocking element 12 would have to be moved into the too-narrow slit between contact surface 14 and external wall 28. However, due to the considerable width of the blocking element 12, this is not possible in this direction, which is why the movement is blocked.

Figure 5:
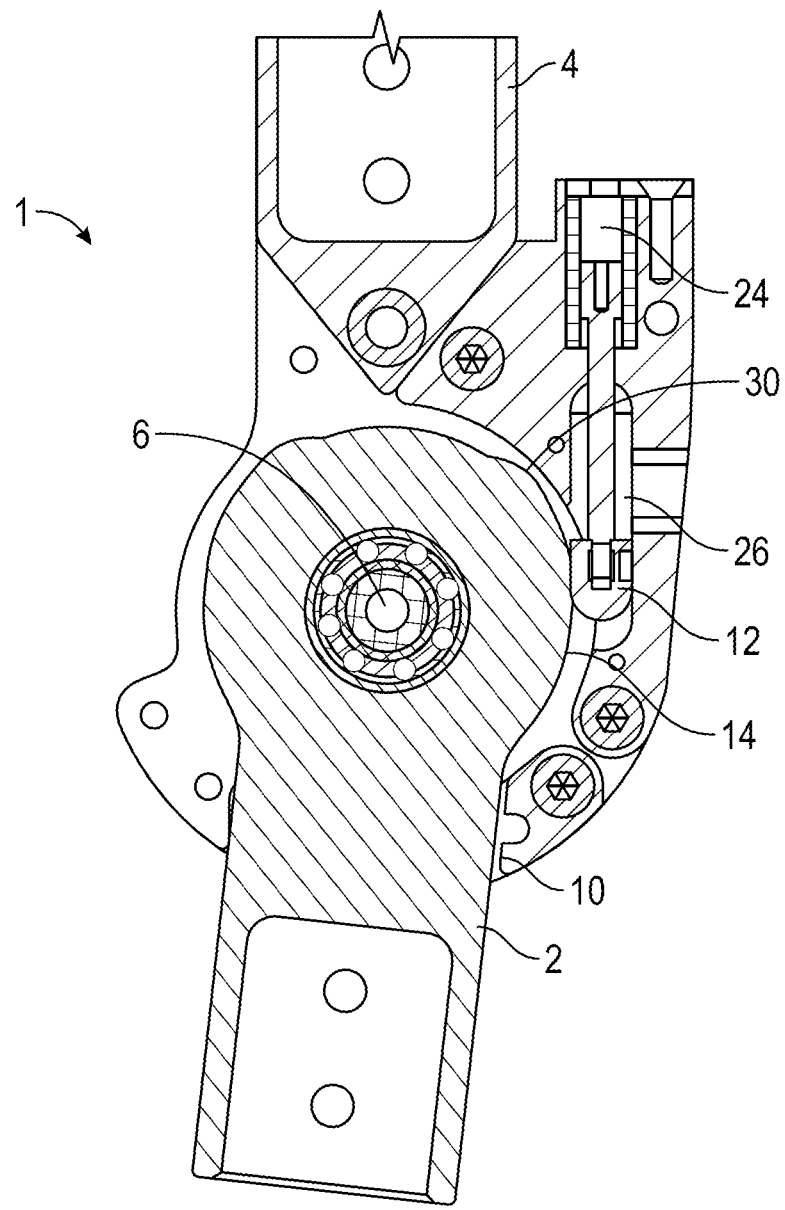

FIG. 5 depicts the joint 1 when almost fully extended. The first articulated arm 2 lies almost flat on the second limit stop 10, which prevents a further swiveling of the first articulated arm 2 relative to the second articulated arm 4 in the direction of extension. The contact surface 14 remains in contact with the blocking element 12 and prevents a swiveling of the first articulated arm 2 relative to the second articulated arm 4 in the direction of flexion in the way previously described in connection with FIG. 4. In contrast to FIG. 5, it is clear that the blocking element 12 has been moved downwards in the guide 26. The spring 24 is considerably loose compared to the situation depicted in FIG. 4. This is achieved as a result of the eccentric design of the contact surface 14. This means that the distance between the contact surface 14 and the swivel axis 6 is also not constant in the area in which the contact surface 14 can come into contact with the blocking element 12. In fact, in the example of an embodiment shown, this distance decreases continuously, starting from a maximum point 30 at which the distance between the contact surface 14 and the swivel axis 6 is at a maximum. In the situation depicted in FIG. 5, the joint 1 is almost completely blocked, as a swiveling of the first articulated arm 2 relative to the second articulated arm 4 is prevented by the second limit stop 10 in the direction of extension and by the blocking element 12 in the direction of flexion.

Figure 6A:
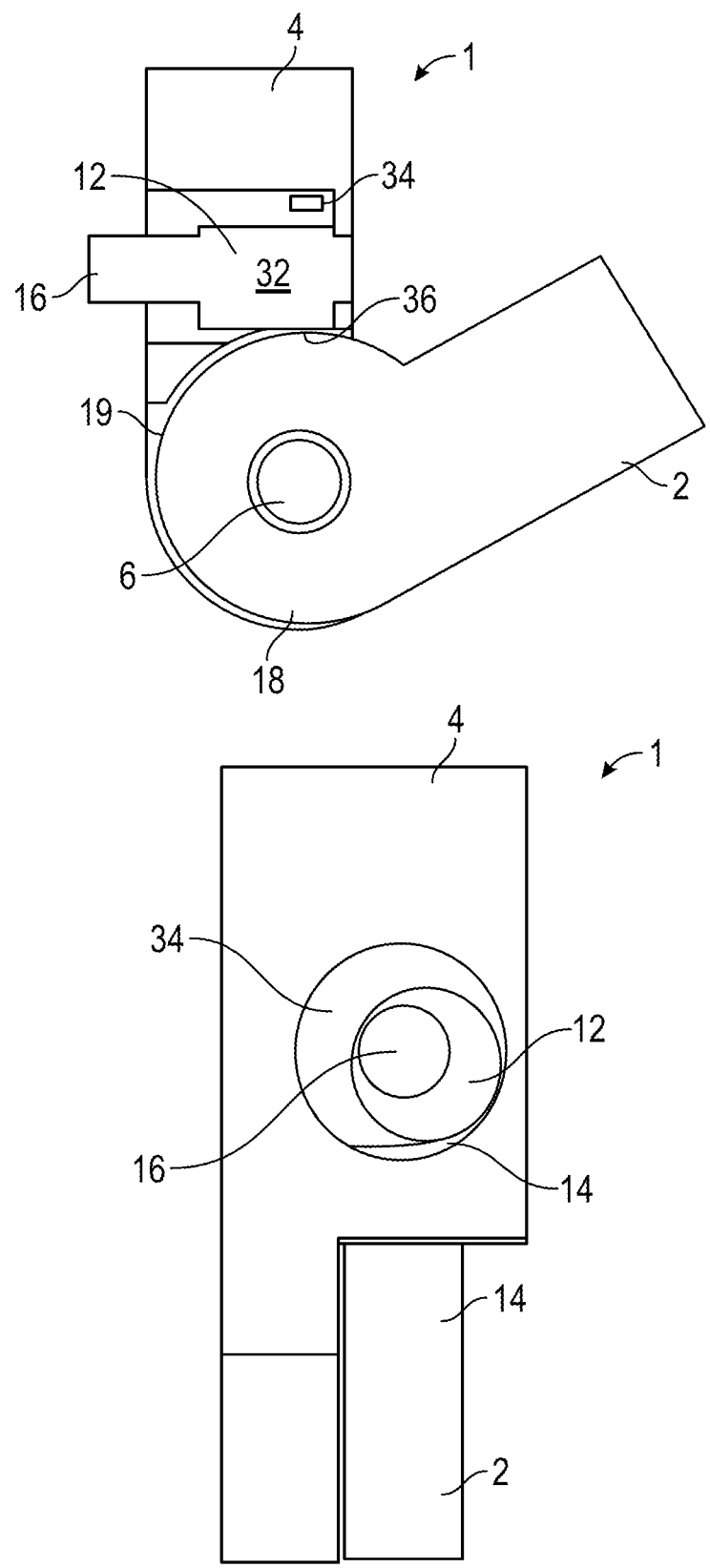
Figure 6B:
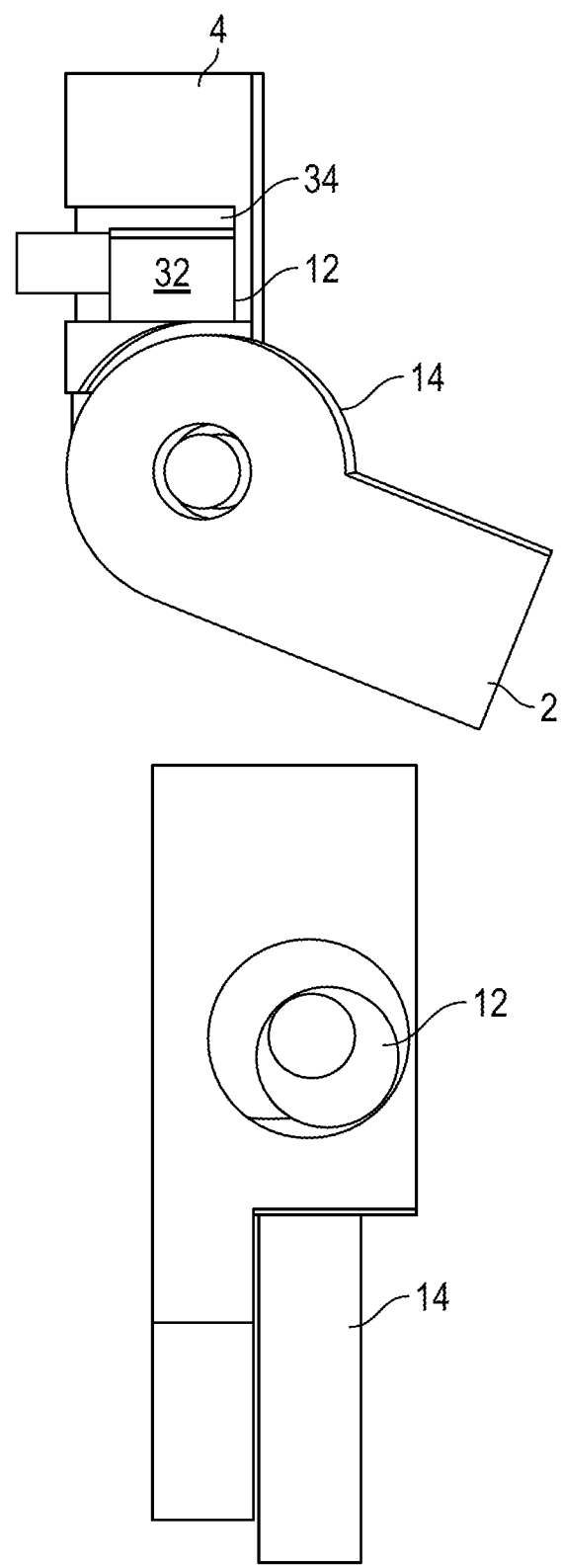
Figure 6C:
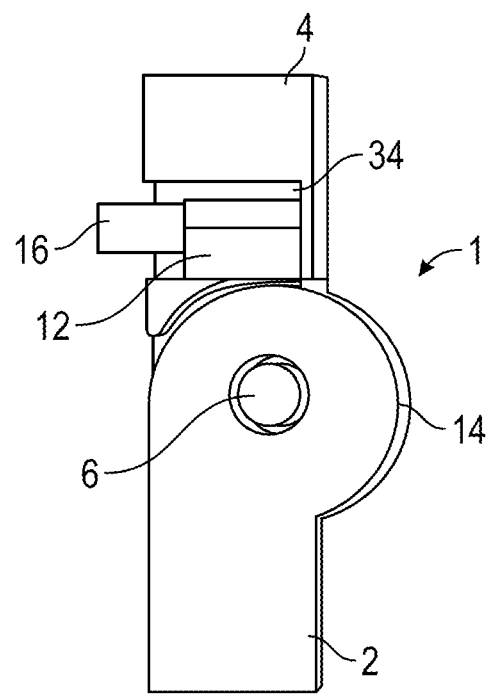
Figure 6C:
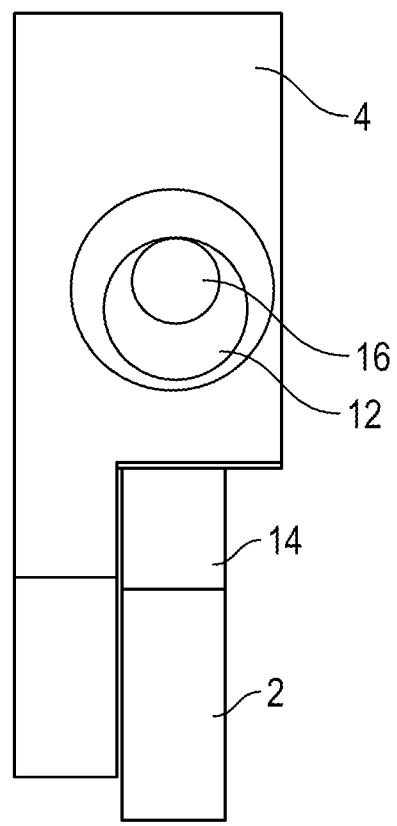

FIGS. 6a to 6c show another embodiment of the joint 1. The left image in each figure shows a sectional view and the right image a lateral view of the joint 1. It comprises the first articulated arm 2, the second articulated arm 4 and the swivel axis 6. The end piece 18 of the first articulated arm 2 features the contact surface 14 on the radially external side and extends around the swivel axis 6. In contrast to the example of an embodiment depicted in FIGS. 1 to 5, the blocking element 12 is shown here as an eccentrically mounted cylinder. It has a lateral surface 32 and is eccentrically mounted, as shown in the right-hand images in FIGS. 6a to 6c for example. In the centre of the extension of the bearing axis of this eccentric mounting is the activation element 16, which in the example of an embodiment depicted is configured to rotate the blocking element 12 about the longitudinal axis of the activation element, which in the example of an embodiment depicted also acts as the bearing axis of the blocking element 12.

The blocking element is situated in a recess 34 that enables such a rotation and features an opening 36 underneath through which the contact surface 14 can protrude into the recess 34.

In the example of an embodiment of the joint 1 shown in FIGS. 6a to 6c, the contact surface 14 is also designed to be eccentric. Once again, this means that the distance between the contact surface 14 and the swivel axis 6 is not constant across the periphery of the end piece 18.

The joint 1 is flexed to a considerable degree in the situation depicted in FIG. 6a: It is an almost complete flexion of the joint 1. The contact surface 14 is designed in such a way that, when in this position, it protrudes as far into the recess 34 as possible, as can be seen particularly clearly in the right-hand image of FIG. 6a. The lateral surface 32 of the blocking element 12 lies flat on the contact surface 14.

Both images in FIG. 6b depict a situation in which the first articulated arm 2 has been swiveled relative to the second articulated arm 4 in the direction of extension. Due to the eccentricity of the contact surface 14, it no longer protrudes so far into the recess 34. It is clear to see that the blocking element 12 has been rotated about the bearing axis as a result, as the lateral surface 32 is still lying flat on the contact surface 14. FIG. 6c depicts the joint 1 when fully extended. The first articulated arm 2 has been swiveled even further relative to the second articulated arm 4, causing the contact surface 14 to no longer protrude into the recess 34, or to only do so to a small extent. In the right-hand image in FIG. 4c in particular it is clear that the blocking element 12 has been rotated about the bearing axis even further, wherein this bearing axis also serves as the longitudinal axis of the activation element 16. In the example of an embodiment shown, this rotation of the blocking element 12 occurs solely as a result of gravity. Of course, a force application element may be provided here that preloads the blocking element 12 in the position shown in FIG. 6c.

In the situation depicted in FIG. 6c, a swiveling of the first articulated arm 2 relative to the second articulated arm 4 about the swivel axis 6 in the direction of flexion, i.e. anti-clockwise, is prevented by the blocking element 12. This type of swiveling would result in the contact surface 14 pushing the blocking element 12 upwards. However, due to the mounting of the blocking element 12 this is not possible given that it would have to accompany a swiveling of the blocking element 12 about the longitudinal axis of the activation element 16, which cannot be achieved by swiveling the two articulated arms 2, 4 relative to one another.

Figure 7:
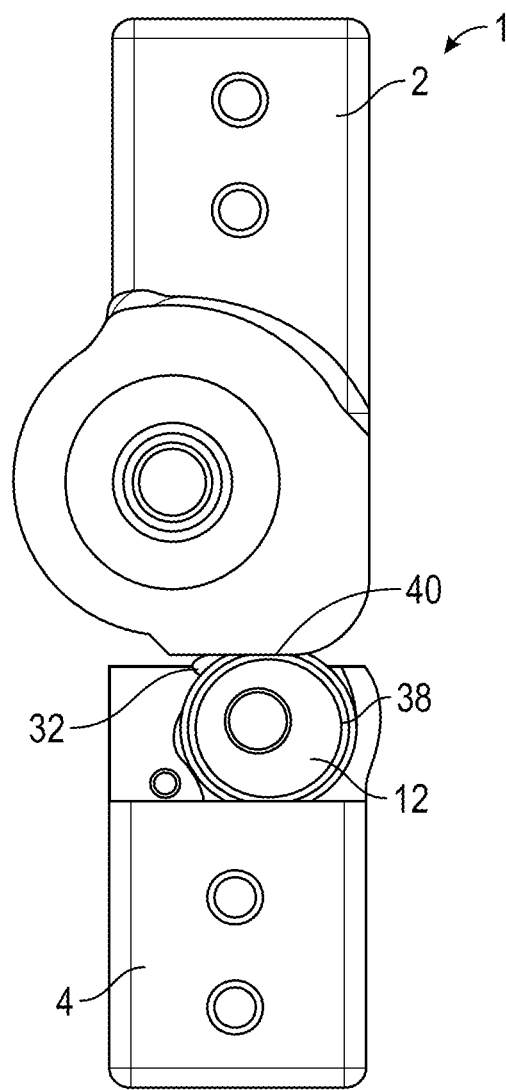

FIG. 7 depicts another joint 1 with the first articulated arm 2 and the second articulated arm 4. The blocking element 12 can be clearly recognized on the second articulated arm 4; the lateral surface 32 of the blocking element interacts with the contact surface 14—not depicted in FIG. 7—of the end piece 18 of the first articulated arm 2. In FIG. 7, it is clear to see that the blocking element 12 features a limit stop lateral surface 38, which is also arranged eccentrically to the rotational axis of the blocking element 12. The positioning of this limit stop lateral surface 38 relative to the lateral surface 32 that comes into contact with the contact surface 14 can be used to adjust the limit stop of the joint 1, i.e. the maximum extension. It is clear to see that a joint limit stop 40 on the first articulated arm 2 in FIG. 7 lies on the limit stop lateral surface 38 and thus prevents a further swiveling of the two articulated arms 2, 4 relative to one another in the direction of extension.

Figure 8:
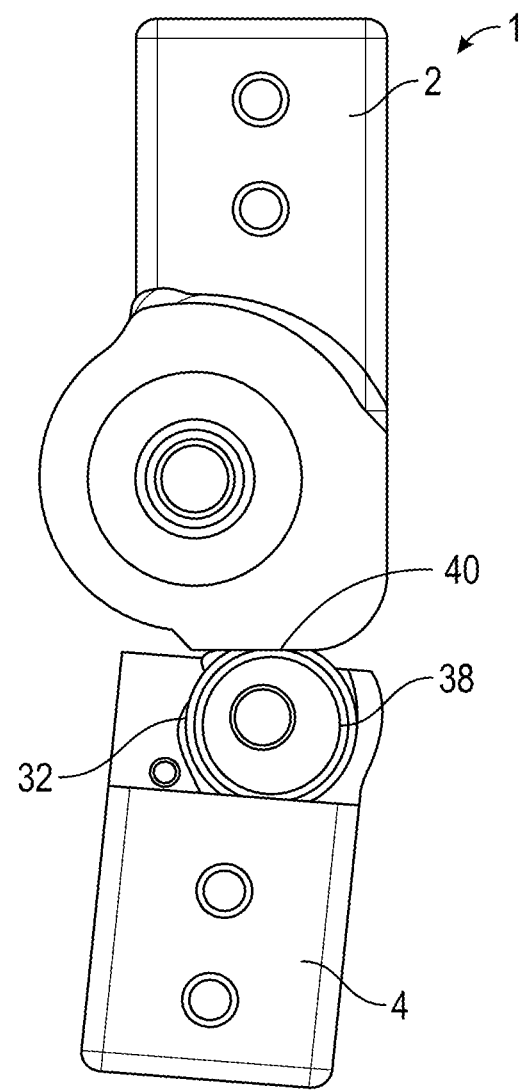

FIG. 8 shows the joint from FIG. 7 wherein the limit stop lateral surface 38 is designed to be twisted relative to the lateral surface 32. This results in the joint limit stop 40 striking the limit stop lateral surface 38 at a different angle between the two articulated arms 2, 4, thereby restricting the extension of the joint 1 in the direction of extension. In the example of an embodiment shown, the stop angle of the joint depicted in FIG. 1 has been moved by 5° compared to the joint 1 shown in FIG. 7.

FIGS. 9a and 9b both show a view of a joint 1 with the blocking element 12 in the embodiment that has already been described. However, the joint 1 also comprises a second blocking device 42 which has a second blocking element 44. It features a second lateral surface 46 that is in contact with and interacts with the contact surface 40. Alternatively to the embodiment shown, two separate contact surfaces 14 may be provided. Whereas the first blocking device with the blocking element 12 prevents a swiveling of the two articulated arms 2, 4 in the first swivel direction, insofar as the swivel angle between the two articulated arms 2, 4 lies within a predetermined range, the second blocking device 42 prevents a swiveling of the two articulated arms 2, 4 in the second swivel direction, which is in the opposite direction to the first swivel direction. However, a swiveling in this second swivel direction is only prevented insofar as the swivel angle is within the second predetermined range.

In FIG. 9b, it is clear to see that the two blocking elements 12, 44 are arranged at an offset to one another. This renders it especially easy to achieve the positioning of the two contact surfaces 14, one of which is arranged on the first articulated arm 2 and the other on the second articulated arm 4. Selecting the shape of the contour of these contact surfaces 14 renders it possible to determine the swivel behavior of the joint 1.

The invention claimed is:

1. A joint for an orthopedic device, comprising:
   a first articulated arm and a second articulated arm, which are mounted about a swivel axis such that they can be swiveled relative to one another; and
   a blocking device, which can be moved into a release position and a blocking position, wherein the blocking device, when in the blocking position, blocks the swiveling of the first articulated arm relative to the second articulated arm in a first swivel direction and allows the swiveling in a second swivel direction, independently of a swivel angle between the first articulated arm and the second articulated arm, insofar as the swivel angle is in a predetermined range, and allows the swiveling in the first swivel direction, insofar as the swivel angle is outside of the predetermined range; and wherein a contact surface is arranged on the first articulated arm, which comes into contact with a blocking element, which blocking element is moveably arranged on the second articulated arm, when the blocking device is in the blocking position, and wherein the contact between the blocking element and the contact surface blocks swiveling of the first articulated arm relative to the second articulated arm in the first swivel direction.

2. The joint according to claim 1, wherein the blocking element is a cam mounted in a guide such that cam can be moved, or the blocking element is an eccentrically mounted pin, bolt or cylinder.

3. The joint according to claim 1, wherein the blocking element is preloaded towards the contact surface.

4. The joint according to claim 1, wherein the blocking element is preloaded by a spring or a weight force acting on the blocking element.

5. The joint according to claim 1, wherein the contact surface is designed to be eccentric relative to the swivel axis.

6. The joint according to claim 1, further comprising an activation element, the activation of which enables movement of the blocking device from the blocking position into the release position.

7. The joint according to claim 1, wherein a swivel range in which the first articulated arm can be swiveled relative to the second articulated arm extends from a first limit stop to a second limit stop, the predetermined range being smaller than the swivel range and, the predetermined range in the second swivel direction is restricted by the second limit stop, the second swivel direction being opposite the first swivel direction.

8. The joint according to claim 1, further comprising a second blocking device which can be moved into a release position and a blocking position, in which the second blocking device blocks the swiveling of the first articulated arm relative to the second articulated arm in the second swivel direction, which is opposite the first swivel direction, independently of a swivel angle between the first articulated arm, and the second articulated arm, insofar as the swivel angle is in a predetermined range, and allows the swiveling in the second swivel direction, insofar as the swivel angle is outside of the predetermined range.

9. A joint for an orthopedic device, comprising:
a first articulated arm mounted about a swivel axis;
a second articulated arm mounted about the swivel axis and configured to swivel relative to the first articulated arm; and a blocking device movable into a blocking position to block swiveling of the first articulated arm relative to the second articulated arm in a first swivel direction and to allow swiveling in a second swivel direction when a swivel angle between the first and second articulated arms is within a predetermined range, and allows swiveling of the first articulated arm relative to the second articulated arm when the swivel angle is outside of the predetermined range, the blocking device being movable independent of the swivel angle; and further comprising a blocking element moveably arranged on the second articulated arm, wherein the first articulated arm includes a contact surface arranged to contact the blocking element when the blocking device is in the blocking position, wherein contact between the blocking element and the contact surface blocks swiveling of the first articulated arm relative to the second articulated arm in the first swivel direction.

10. The joint according to claim 9, wherein the blocking element is a cam mounted in a guide such that cam can be moved, or the blocking element is an eccentrically mounted pin, bolt or cylinder.

11. The joint according to claim 9, wherein the blocking element is preloaded towards the contact surface.

12. The joint according to claim 9, wherein the blocking element is preloaded by a spring or a weight force acting on the blocking element.

13. The joint according to claim 9, wherein the contact surface is eccentric relative to the swivel axis.

14. The joint according to claim 9, further comprising an activation element, the activation of which enables movement of the blocking device from the blocking position into a release position.

15. The joint according to claim 9, wherein a swivel range in which the first articulated arm can be swiveled relative to the second articulated arm extends from a first limit stop to a second limit stop, the predetermined range being smaller than the swivel range, and the predetermined range in the second swivel direction is restricted by the second limit stop, the second swivel direction being opposite the first swivel direction.

16. The joint according to claim 9, further comprising a second blocking device movable into a blocking position to block swiveling of the first articulated arm relative to the second articulated arm in the second swivel direction, which is opposite the first swivel direction when the swivel angle is in the predetermined range, and allows the swiveling in the second swivel direction when the swivel angle is outside of the predetermined range, the second blocking device being movable independent of the swivel angle.

* * * * *